(12) United States Patent
Chapman

(10) Patent No.: US 7,330,530 B2
(45) Date of Patent: Feb. 12, 2008

(54) DIFFRACTION ENHANCED IMAGING METHOD USING A LINE X-RAY SOURCE

(75) Inventor: Leroy Dean Chapman, Saskatoon (CA)

(73) Assignee: Illinois Institute of Technology, Chicago, IL (US)

( * ) Notice: Subject to any disclaimer, the term of this patent is extended or adjusted under 35 U.S.C. 154(b) by 0 days.

(21) Appl. No.: 10/957,884

(22) Filed: Oct. 4, 2004

(65) Prior Publication Data

US 2006/0072702 A1   Apr. 6, 2006

(51) Int. Cl.
*G21K 1/06* (2006.01)
*G01T 1/36* (2006.01)

(52) U.S. Cl. .............................. 378/85; 378/82; 378/84
(58) Field of Classification Search .................. 378/71, 378/84, 85, 70, 82
See application file for complete search history.

(56) References Cited

U.S. PATENT DOCUMENTS

| 2,543,630 | A | 2/1951 | Hansen |
|---|---|---|---|
| 2,853,617 | A | 9/1958 | Berreman |
| 3,032,656 | A | 5/1962 | Hosemann et al. |
| 3,439,163 | A | 4/1969 | DeJongh |
| 3,628,040 | A | 12/1971 | Schnopper et al. |
| 3,777,156 | A | 12/1973 | Hammond et al. |
| 3,885,153 | A | 5/1975 | Schoenborn et al. |
| 4,223,219 | A | 9/1980 | Born et al. |
| 4,351,063 | A | 9/1982 | Dineen et al. |
| 4,599,741 | A | 7/1986 | Wittry |
| 4,625,323 | A | 11/1986 | Okaya |
| 4,649,557 | A | 3/1987 | Hornstra et al. |
| 4,737,973 | A | 4/1988 | Ogawa et al. |
| 4,949,367 | A | 8/1990 | Huizing et al. |
| 5,123,036 | A | 6/1992 | Uno et al. |
| 5,127,028 | A | 6/1992 | Wittry |
| 5,164,975 | A | 11/1992 | Steinmeyer |
| 5,195,115 | A | 3/1993 | Schiller et al. |
| 5,245,648 | A | 9/1993 | Kinney et al. |

(Continued)

FOREIGN PATENT DOCUMENTS

WO          95/05725          2/1995

OTHER PUBLICATIONS

D. Chapman, W. Thomlinson, R.E. Johnson, D. Washburn, E. Pisano. N. Gmür, Z. Zhong, R. Menk, F. Arfelli and D. Sayers, *X-Ray Refraction Imaging (XRI) Applied to Mammography*, published Oct. 31, 1997.

(Continued)

*Primary Examiner*—Chih-Cheng G Kao
(74) *Attorney, Agent, or Firm*—Pauley Petersen & Erickson

(57) ABSTRACT

A method for detecting an enhanced image of an object by independently analyzing, detecting, digitizing, and combining images acquired on a high and a low angle side of a rocking curve of a crystal analyzer. An x-ray beam generated by a line x-ray source is collimated by a crystal monochromator including two non-matching crystals to form an x-ray area beam. The x-ray area beam is transmitted through an object to be imaged and onto an image detector and the image is digitized. The digitized images are simultaneously solved, preferably on a pixel-by-pixel basis, to derive an enhanced image which has dramatically improved contrast and spatial resolution over an image acquired through conventional radiology methods.

17 Claims, 3 Drawing Sheets

U.S. PATENT DOCUMENTS

| | | | |
|---|---|---|---|
| 5,259,013 | A | 11/1993 | Kuriyama et al. |
| 5,319,694 | A | 6/1994 | Ingal et al. |
| 5,406,609 | A | 4/1995 | Arai et al. |
| 5,428,657 | A | 6/1995 | Papanicolopoulos et al. |
| 5,457,726 | A | 10/1995 | Miyazaki |
| 5,457,727 | A | 10/1995 | Frijlink |
| 5,579,363 | A | 11/1996 | Ingal et al. |
| 5,715,291 | A | 2/1998 | Momose |
| 5,717,733 | A | 2/1998 | Kurbatov et al. |
| 5,787,146 | A | 7/1998 | Giebeler |
| 5,802,137 | A | 9/1998 | Wilkins |
| 5,805,662 | A | 9/1998 | Kurbatov et al. |
| 5,850,425 | A | 12/1998 | Wilkins |
| 5,923,720 | A | 7/1999 | Barton et al. |
| 5,949,847 | A | 9/1999 | Terada et al. |
| 5,987,095 | A | 11/1999 | Chapman et al. |
| 6,035,227 | A | 3/2000 | Shmueli |
| 6,038,285 | A | 3/2000 | Zhong et al. |
| 6,269,144 | B1 | 7/2001 | Dube et al. |
| 6,385,289 | B1 | 5/2002 | Kikuchi |
| 6,577,708 | B2 | 6/2003 | Chapman et al. |
| 6,804,324 | B2 | 10/2004 | Martynov et al. |
| 2002/0136352 | A1 | 9/2002 | Protopopov |
| 2004/0196957 | A1 | 10/2004 | Ando |

OTHER PUBLICATIONS

V.N. Ingal and E.A. Beliaevskaya, *Phase Dispersion Introscopy*, (published prior to Oct. 16, 1996).

V.N. Ingal and E.A. Beliaevskaya, X-ray plane-wave topography observation of the phase contrast from a non-cystalline object, *J. Phys. D: Appl. Phys.* 28 (995) 2314-2317.

V.N. Ingal and E.A. Belyaevskaya, Method of phase-dispersion introscopy, *Tech. Phys.* 42 (1), Jan. 1997.

V.N. Ingal and E.A. Beliaevskaya, Phase dispersion radiography of biological objects, *Physica Medica*, vol. X11, No. 2, Apr.-Jun. 1996.

V.A. Bushuev, V.N. Ingal and E.A. Belyaevskaya, Dynamical Theory of Images Generated by Noncrystalline Objects for the Method of Phase-Dispersive Introscopy, *Crystallography Reports*, vol. 41, No. 5, 1996, pp. 766-774.

V.A. Bushuev, E.A. Beliaevskaya and V.N. Ingal, *Wave-optical description of X-ray phase contrast images of weakly absorbing non-crystalline objects*, II Nuovo Cimento, vol. 19D, No. 2-4, Feb.-Apr. 1997.

V.N. Ingal and E.A. Beliaevskaya, *Imaging of biological objects in the plane-wave diffraction scheme*, II Nuovo Cimento, vol. 19D, No. 2-4, Feb.-Apr. 1997.

V.N. Ingal and E.A. Beliaevskaya, Phase Dispersion Introscopy, *Surface Investigation*, vol. 12, pp. 441-450, 1997.

Tetsuya Ishikawa, Seishi Kikuta and Kazutaka Kohra, Angle-Resolved Plane Wave X-Ray Topography, *Japanese Journal of Applied Physics*, vol. 24, No. 7, Jul. 1985, pp. L559-L562.

R.C. Blasdell and A.T. Macrander, Prototype grooved and spherically bent Si backscattering crystal analyzer for meV resolution inelastic x-ray scattering, *Review of Scientific Instruments*, vol. 66, No. 2, Feb. 1995, pp. 2075-2077, New York.

Monochromatic energy-subtraction radiography using a rotating anode source and a bent Laue monochromator, a paper published in *Phys. Med. Biol.*, 42 (1997), pp. 1751-1762.

A bent Laue crystal monochromator for monochromatic radiography with an area beam, a paper published in *Nuclear Instruments and Methods in Physics Research, Section A*, 399 (1997), pp. 489-498.

Kenneth Lange et al.: EM Reconstruction Algorithms for Emission and Transmission Tomography, *Journal of Computer Assisted Tomography*, pp. 306-316, 1984.

A.P. Dempster et al.: *Maximum Likelihood from Incomplete Data via the EM Algorithm*, pp. 1-38, 1976.

Hasnah et al.: Diffraction Enhanced Imaging Contrast Mechanisms in Breast Cancer Specimens, *Medical Physics 29*, pp. 2216-2221, 2002.

J.L. Cronin in Modem dispenser cathodes, *IEE Proc.*, vol. 128, Pt. 1, No. 1, (Feb. 1981).

DIFFRACTION ENHANCED IMAGING METHOD USING A LINE X-RAY SOURCE

This work was supported in part by U.S. Army Medical Research and Material Command grant DAMD 17-99-1-9217 and State of Illinois Higher Education Cooperative Agreement.

FIELD OF THE INVENTION

This invention relates to a method for detecting an image of an object, such as one mass internal with respect to another mass wherein the one mass has an absorption content, refraction content, and/or density content different from the other mass. The method of this invention measures the intensity of an x-ray beam, such as an area x-ray beam, as it emits from an object, preferably as a function of angle, and derives an enhanced image from the measured intensity.

BACKGROUND OF THE INVENTION

X-ray imaging has been used in the medical field and for radiology in general, such as non-destructive testing and x-ray computed tomography. Conventional radiography systems use x-ray absorption to distinguish differences between different materials, such as normal and abnormal human tissues.

Conventional x-ray radiography measures the projected x-ray attenuation, or absorption, of an object. Attenuation differences within the object provide contrast of embedded features that can be displayed as an image. For example, cancerous tissues generally appear in conventional radiography because these tissues are more dense than the surrounding non-cancerous tissues. The best absorption contrast is generally obtained at x-ray energies where the absorption is high. Conventional radiography is typically performed using lower x-ray energy in higher doses to allow greater absorption and, thus, better contrast and images. In general, as the x-ray energy level increases and the x-ray dose used decreases, the quality of the conventional radiography image lessens.

Diffraction Enhanced Imaging (DEI), for example, as disclosed in U.S. Pat. No. 5,987,095, issued to Chapman et al., and U.S. Pat. No. 6,577,708, issued to Chapman et al., is an x-ray radiographic technique that derives contrast from x-ray refraction and scatter rejection (extinction) in addition to the absorption of conventional radiography. DEI can be used to detect, analyze, combine and visualize the refraction, absorption and scattering effects upon an image of an object. DEI is particularly useful for relatively thick and thus highly absorbing materials. Compared to the absorption contrast of conventional radiography, the additional contrast mechanisms, refraction and scatter, of DEI allow visualization of more features of the object.

DEI can use highly collimated x-rays prepared by x-ray diffraction from monochromator crystals. These collimated x-rays are of single x-ray energy, practically monochromatic, and are used as the x-ray beam to image an object. Once this x-ray beam passes through the object, a crystal analyzer is introduced. If the crystal analyzer is rotated about an axis, for example, the axis perpendicular to the plane shown in FIG. 1, the crystal will rotate through a Bragg condition for diffraction and the diffracted intensity will trace out a profile that is called the rocking curve. The profile will be roughly triangular and will have peak intensity close to that of the beam intensity striking the analyzer crystal. The width of the profile is typically a few microradians wide, for example 3.6 microradians within a full width of half maximum (FWHM) at 18 keV using a silicon (3, 3, 3) reflection. The character of the images obtained change depending on the setting of the analyzer crystal. To extract refraction information, the analyzer is typically set to the half intensity points on low and high angle sides of the rocking curve. At least two intensity images are obtained by a detector at different angled positions, for example, one at each of the low and high angle sides of the rocking curve, of the crystal analyzer. The intensity images are mathematically combined to obtain enhanced images, such as a refraction angle image.

Current DEI methods are typically performed using a synchrotron x-ray source and an object scanning system that moves the object through the collimated x-ray beam. There is a need for an imaging method that provides an area image without an object scanning system. There is a need for a DEI imaging method that can utilize conventional x-ray sources, and, more particularly, relatively higher x-ray tube power than generally used with conventional x-ray radiography to reduce imaging time.

SUMMARY OF THE INVENTION

It is one object of this invention to provide a method for detecting an image of an object and using the image to determine differences in the composition of matter and/or structural arrangement of the object.

It is another object of this invention to provide a method for detecting an image of an object using a line x-ray source.

It is yet another object of this invention to provide a method for detecting an area image of an object using an area x-ray beam.

The above and other objects of this invention are accomplished with a method that irradiates an x-ray beam, such as a mono-energetic beam, through an object and directs a transmitted beam, which is emitted from the object, at an angle of incidence upon a crystal analyzer. A diffracted beam emitted from the crystal analyzer is used to detect an intensity image of the object. Intensity images are detected at least at two positions of the crystal analyzer, and then the images are mathematically combined to derive an enhanced image of the object.

The method of this invention is a DEI method in that the method uses highly collimated x-rays prepared by x-ray diffraction from monochromator crystals. These collimated x-rays are of single x-ray energy, practically monochromatic, and are used as the beam to image an object. In the method of one embodiment of this invention, the collimated x-rays originate from a line x-ray source and are prepared by a set of non-matching crystals of a crystal monochromator to form an x-ray area beam. Once this area beam passes through the object, another crystal is introduced. This crystal is called the crystal analyzer. If this crystal analyzer is rotated about an axis, the crystal will rotate through the Bragg condition for diffraction and the diffracted intensity will trace out a profile that is called the rocking curve. The profile will be roughly triangular and will have peak intensity close to that of the beam intensity striking the analyzer crystal. The width of the profile is typically a few microradians wide. The character of the images obtained changes depending on the setting of the analyzer crystal. To extract refraction information, the analyzer is typically set to the half intensity points on the low and high angle sides of the rocking curve. For optimal scatter rejection sensitivity, the analyzer is typically set to the peak of the rocking curve. To image the rejected scatter, the analyzer is typically set in the wings of the rocking curve.

The imaging method according to this invention allows a line x-ray source to be used in DEI methods. Using a line x-ray source allows for area images to be obtained, thereby avoiding the more complicated scanning system, and the associated moving parts, currently used with typical DEI methods. A line x-ray source also allows a relatively higher x-ray tube power, as compared to conventional radiography, to be used, thereby reducing the imaging time and x-ray exposure. The method according to this invention works with either a Laue type crystal analyzer, which is a transmission type analyzer, or a Bragg type crystal analyzer, which is a reflection type analyzer.

BRIEF DESCRIPTION OF THE DRAWINGS

The above-mentioned and other features and objects of this invention will be better understood from the following detailed description of preferred embodiments taken in conjunction with the drawings.

DETAILED DESCRIPTION OF THE PRESENTLY PREFERRED EMBODIMENTS

The imaging method of his invention is a type of Diffraction Enhanced Imaging (DEI). The imaging method of this invention is different from other DEI methods, such as, for example, the x-ray imaging method disclosed in U.S. Pat. No. 5,987,095 issued to Chapman et al. and/or in U.S. Pat. No. 6,577,708 issued to Chapman et al., the entire disclosures of which are incorporated into this specification by reference, in that this imaging method uses a line x-ray source and non-matching monochromator crystals to prepare an x-ray imaging area beam for obtaining an area image of an object. The non-matching crystals of the crystal monochromator allow the use of a line x-ray source.

Figure 1:
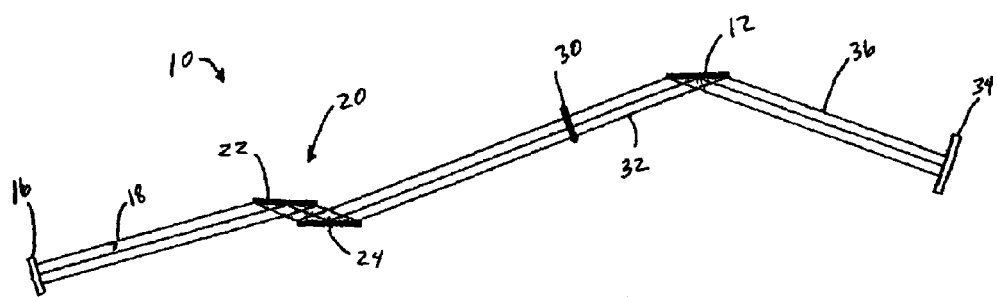
FIG. 1 is a schematic diagram of a crystal analyzer system including a Bragg type crystal analyzer, according to one preferred embodiment of this invention.

FIG. 1 shows a schematic diagram of analyzer system 10, according to one preferred embodiment of this invention. The analyzer system 10 includes a crystal analyzer 12. The crystal analyzer 12 represents a Bragg type crystal analyzer. As will be appreciated by those skilled in the art following the teachings herein provided, a Laue type analyzer can also be used in the method of this invention for analysis purposes.

The analyzer system and imaging method of this invention use an x-ray beam generated from an x-ray source, or target, to detect an image of an object. In the embodiment of the invention shown in FIG. 1, the x-ray source is a line x-ray source 16. The line x-ray source 16 generates x-ray beam 18. In one embodiment of this invention the line x-ray source includes molybdenum. Using a line x-ray source in the imaging method of this invention to prepare an area beam for imaging the object allows for use of generally higher x-ray tube power, as compared to conventional x-ray radiography, and reduced imaging time. According to one preferred embodiment of this invention, x-ray beam 18 has an energy level in a range of approximately 10 keV to approximately 100 keV, and desirably approximately 16 keV to approximately 40 keV.

The x-ray beam 18 is diffracted by a crystal monochromator 20 before transmitting through an object 30. The crystal monochromator 20 includes non-matching monochromator crystals 22 and 24. As shown in FIG. 1, the x-ray beam 18 is first diffracted by a first monochromator crystal 22 toward a second monochromator crystal 24. The x-ray beam 18 is diffracted by the second monochromator crystal 24 toward the object 30. The monochromator crystals 22 and 24 are non-matching in that the first monochromator crystal 22 is different from the second monochromator crystal 24 in at least one of lattice spacing or crystal type. In the analyzer system 10, the x-rays emitted from the line x-ray source 16 are diffracted by the crystal monochromator 20 and collimated to within the rocking curve width of the second monochromator crystal 24. The x-rays of the x-ray beam 18 diverge in the vertical plane, giving rise to the area beam emitted through the object 30.

The use of a line x-ray source in combination with the non-matching crystals 22 and 24 of the crystal monochromator 20 provides particular benefits over the typical DEI methods practiced using a synchrotron x-ray source. The method of this invention forms an x-ray area beam that provides an area beam of the object 30, thereby increasing the stability of the analyzer system 10 and eliminating the moving parts of current scanning systems. The line x-ray source allows relatively higher x-ray power to be used with conventional x-ray tubes. In addition, the mismatched crystal monochromator of this invention can eliminate unwanted x-ray photon energies from the x-ray imaging beam.

The x-ray beam 18 is transmitted through the object 30. A transmitted x-ray beam 32 that emits from the object 30 is directed at an angle of incidence upon the crystal analyzer 12. The crystal analyzer 12 is preferably positioned between the object 30 and a detector 34. The crystal analyzer 12 is preferably fixed spatially with respect to the transmitted x-ray beam 32, and oriented to diffract the transmitted x-ray beam 32 onto the detector 34. Fine angular control of crystal analyzer 30 can be accomplished with a stepper motor driven translation stage pushing on a relatively long rod which is mechanically connected to an axle onto which the crystal analyzer 12 is attached. The fine angular control may result in a resolution limit of approximately 1 microradian. Such fine tuning can position the crystal analyzer 12 at various positions within the rocking curve of the crystal analyzer 12.

In one embodiment of the invention, an enhanced image of the object 30 is derived by combining at least two images of the object 30 detected at different angular position of the crystal analyzer 12. A first image of the object 30 is detected from a diffracted beam 36 emitted from the crystal analyzer 12 at a first angular position of the crystal analyzer 12. A second image of the object 30 from a diffracted beam 36 emitted from the crystal analyzer at a second angular position of the crystal analyzer 12.

The first and second angular positions of the crystal analyzer 12 are desirably within a rocking curve of the crystal analyzer 12. The rocking curve of the crystal analyzer 12 is the sensitivity function of the analyzer system 10 and is characterized by the x-ray output as a function of the angular position of analyzer system 10 when no object is present in x-ray beam 18, as prepared by the monochromator 20. In one embodiment of the invention, the first image of the object 30 is detected at a low rocking curve angle setting of the crystal analyzer 12 and the second image of the object 30 is detected at a high rocking curve angle setting of the crystal analyzer 12. The first and second images are desirably exposed on a detector capable of producing a digitized image. The exposed first and second images can be digitized and mathematically combined to form the enhanced image. The method of this invention can be used to form any enhanced image that other DEI methods can produce. In one embodiment of the invention the enhanced image is an absolute absorption image or a refraction image.

Any suitable detector known to those skilled in the art can be used to detect an image of object 30. In one preferred embodiment according to this invention, an area image of the object 30 is detected with an image plate which comprises a photo-stimulable phosphor image plate typically used for radiology, such as FUJI Medical Systems high resolution HR5 and standard resolution ST5 image plates. An image recorded on the image plate can be digitized, stored and displayed, for example by a FUJI Medical Systems AC3 reader and workstation or by any other suitable digital conversion means known to those skilled in the art. A suitable spatial resolution of images can be 0.1×0.1 mm². The digitized images can then be mathematically combined to form the enhanced image of this invention.

In one embodiment of the invention, a first image ($I_L$) of the object 30 is detected at a low rocking curve angle setting of the crystal analyzer 12 and a second image ($I_H$) of the object 30 is detected at a high rocking curve angle setting of the crystal analyzer 12. Both the first and second images $I_L$ and $I_H$ have a similar absorption content, but a sensitivity to refraction effects is reversed between both images $I_L$ and $I_H$. A sensitivity to refraction occurs because crystal analyzer 12 has a relatively steep intensity versus angle dependence. The first and second images are desirably images exposed on a detector capable of producing a digitized image. The exposed first and second images can be digitized and mathematically combined to form the enhanced image.

The first image $I_L$ and the second image $I_H$ acquired with either a Bragg type or a Laue type crystal analyzer 12, represent independent measurements of the combined absorption and refraction properties of the object 30. It should be noted that there is a distinction between refraction and scattering. Refraction occurs from long range spatial variations in a density and/or thickness of a material. In one preferred embodiment according to this invention, a range of refraction angles used in experimentation was less than approximately 1 microradian. Scattering occurs when a material is structured on a length scale smaller than the resolution of the detector (typically some 10's of microns), down to length scales comparable to the wavelength of the x-rays. Any ordered arrangement within the object 30 that scatters x-rays with an angle greater than a few microradians will likely be rejected by the crystal analyzer 12. Thus, any scattering due to order in the material of the object 30 will reduce a diffracted intensity and will appear in the image as an apparent absorption. Such effect allows for image contrast based on scattering by, as well as absorption of, the material of the object 30.

The arrangement of the analyzer system 10 according to this invention allows a sensitivity to refraction effects along a direction in which the crystal analyzer 12 diffracts the transmitted beam 32. Such direction represents a scan direction which was used in experimental measurements according to one preferred embodiment of the method of this invention. Thus, according to one preferred embodiment of this invention, analyzer system 10 is sensitive to refraction effects in such direction. If such direction is arbitrarily chosen to be the z direction, then an angle of x-rays deviated by the object 30 in the z direction is denoted by $\delta_z$. Such small deviation angles tend to redirect x-rays transmitted through the crystal analyzer 12 and also tend to modulate an intensity diffracted by the Bragg type crystal analyzer 12, according to the rocking curve value. If the crystal analyzer 12 is set for one-half of the maximum intensity, then small deviation angles will modulate the intensity above and below the half intensity values. The sensitivity to small deviation angles can be determined by a local slope of the rocking curve. The intensity I recorded in the image is the combination of such two effects, as shown below in Equation 1.

$$I = I_T\left(R + \frac{\delta R}{\delta\theta}\delta_Z\right) \quad \text{Equation 1}$$

The intensity I is the diffracted beam intensity recorded on detector 34. The intensity $I_T$ is the intensity which is transmitted through the object 30. If imaged alone, the intensity $I_T$ would be the normal absorption image of the object 30. The reflectivity R of the crystal analyzer 12 was set at approximately 0.5 for the one-half intensity point, according to experimentation conducted. The gradient term $\delta R/\delta\theta$ is the local slope of the rocking curve at a set position of the crystal analyzer 12, and is used to determine an intensity modulation created by refraction of the x-rays along the z direction in the object 30.

When the same object 30 is imaged at two angular settings of the crystal analyzer 12, for example, on each side of the rocking curve, Equations 2 and 3 are used to determine an intensity which is preferably recorded on each pixel of the detector 34 for each image acquired.

$$I_H = I_T\left(R_H + \left(\frac{\delta R}{\delta\theta}\right)_H \delta_Z\right) \quad \text{Equation 2}$$

$$I_L = I_T\left(R_L + \left(\frac{\delta R}{\delta\theta}\right)_H \delta_Z\right) \quad \text{Equation 3}$$

Intensities $I_L$ and $I_H$ correspond to low rocking curve angle and high rocking angle image pixel values, respectively. Equations 2 and 3 can be solved for the normal absorption image $I_T$ and the refraction angle image $\delta_Z$, as shown in Equations 4 and 5.

$$I_T = \frac{I_L\left(\frac{\delta R}{\delta\theta}\right)_H - I_H\left(\frac{\delta R}{\delta\theta}\right)_L}{R_L\left(\frac{\delta R}{\delta\theta}\right)_H - R_H\left(\frac{\delta R}{\delta\theta}\right)_L} \quad \text{Equation 4}$$

-continued $$\delta_Z = \frac{I_L R_H - I_H R_L}{I_L \left(\frac{\delta R}{\delta \theta}\right)_H - I_H \left(\frac{\delta R}{\delta \theta}\right)_L}$$ Equation 5

Equations 4 and 5 are used to compute and combine the low rocking curve angle image and the high rocking curve angle image into refraction and absorption images. While the method of this invention can use an area x-ray beam to create an area image on the detector 34, the algorithm is preferably applied to the pixilated detector image on a pixel-by-pixel basis on raw data images which are aligned so that each pixel in each image is from a same region in imaged object 30.

The absorption image provided by the method of this invention differs from a normal transmitted image according to conventional radiography technology, which does not use a crystal analyzer, in that the absorption image contains nearly no scatter from imaged object 30, primarily due to extremely tight conditions imposed by a Bragg type scattering condition. Any rays which are deviated by even a few microradians from a direct path and/or which are deviated in energy by a few electron volts, such as $\Delta E/E \geq 10^{-4}$, will not be diffracted by crystal analyzer 12. Such arrangement will remove relatively small angle scattering and other forms of coherent scattering, and will also remove Compton scattering. Both types of scattering mechanisms contribute to loss of contrast in imaging. Thus, diffracted beam images are almost completely scatter-free.

The method according to this invention can be conducted with either a Bragg type crystal analyzer or a Laue type crystal analyzer. A Bragg type system uses reflection geometry to obtain refraction and absorption images in a near absence of coherent and inelastic scattering. Reflection geometry of the Bragg type system provides a single diffracted beam image at a single setting of crystal analyzer 12. An image produced with a Bragg system provides a refraction angle image of object 30 and a nearly scatter-free absorption image of object 30.

When using a Laue type system, transmission geometry is used to obtain refraction and absorption images in a similar manner as with a Bragg system. However, the Laue system has two main differences over the Bragg system. First, in a Laue system a forward diffracted beam is emitted from the crystal analyzer, in addition to a diffracted beam. The forward diffracted beam produces an image which contains some of the scatter rejected by the diffracted beam image. Information contained within the forward diffracted beam image can be used to detect and image scatter resulting from the transmitted x-ray beam passing through the object. Second, the intensity of the image downstream of the crystal analyzer in a Laue system is not as intensity efficient as in a Bragg system. When the crystal analyzer has an optimal crystal thickness, the diffracted beam is approximately 10% of the beam intensity that it is when striking an entrance side of the crystal analyzer. The efficiency of a Bragg system is approximately 50% or greater than the entrance beam intensity. U.S. Pat. No. 5,987,095 issued to Chapman et al., and herein fully incorporated by reference, further discloses the use of Laue crystals in DEI methods.

The use of non-matching monochromator crystals in the imaging method of this invention allows for use of a line x-ray source. Using a line x-ray source in the imaging method of this invention provides an area x-ray beam that allows area images to be acquired without a scanning system as is presently used with synchrotron based DEI methods. In addition, the line x-ray source allows for use of higher power conventional x-ray tubes as the x-ray source, which can result in reduced imaging time.

In one embodiment of this invention, the non-matching first and second monochromator crystals 22 and 24 differ from each other in at least one of crystal type or crystal lattice spacing. Crystals that differ in "type" differ in the chemical makeup of the crystal, i.e., the chemical element that forms the crystal. For example, a silicon (3,3,3) crystal and a silicon (4,0,0) crystal are of the same crystal type but have different crystal lattice spacings, while a silicon (3,3,3) crystal and a germanium (3,3,3) crystal are different in crystal type and have identical, or at least substantially identical, crystal lattice spacings.

In one particularly preferred embodiment of this invention, the first and second monochromator crystals 22 and 24 are non-matching and the second crystal 24 desirably matches, i.e., is the same crystal type and has the same crystal lattice spacing as, the crystal analyzer 12. In such an embodiment, the first crystal 22 acts as a pre-monochromator, which in conjunction with the crystal 24, serves to eliminate the propagation of undesirable x-ray energies that can fulfill the Bragg requirement and blur the final image. In one presently preferred embodiment of the invention, the first monochromator crystal 22 is constructed of germanium with (3,3,3) lattice planes and the second monochromator crystal 24 and the crystal analyzer 12 are constructed of silicon with (3,3,3) lattice planes.

In another embodiment of the invention, the first monochromator crystal 22 includes a first lattice spacing that is different from a second lattice spacing of the second monochromator crystal 24. As discussed in more detail below with reference to FIGS. 3-5, the range of x-ray wavelength that is accepted by the crystal monochromator 20 is an important parameter for a line x-ray source, as the emission x-rays have a limited range of wavelengths. Therefore, non-matching crystal lattice spacings that may be used in the two crystal monochromator system are generally limited. In one embodiment of the invention, a crystal monochromator including two non-matching monochromator crystals is formed by starting with two crystals identical in type and lattice spacing, such as two silicon (3,3,3) crystal, and heating one of the monochromator crystals to alter the lattice spacing. By heating one of two identical crystals, the mismatch, or difference, between the lattice spacing of the heated crystal and the non-heated crystal can be controlled and be made relatively small to provide the desired wavelength acceptance from the line x-ray source.

The imaging method and the analyzer system of this invention have two aspects that limit the x-ray flux due to the non-matching pair of monochromator crystals. The first flux limiting aspect is a transverse acceptance angle limitation. The traverse acceptance angle (a) can be defined in terms of the Bragg angles ($\theta_1$ and $\theta_2$) of the two non-matching monochromator crystals, the difference between the two Bragg angles ($\Delta\theta$) and the width of acceptance of the two crystals ($\delta\theta$) by Equation 6.

$$a = 2\sin^{-1}\left(\sqrt{\frac{x^2}{2\cos\theta_1}}\right) = 2\sin^{-1}\left(\sqrt{\frac{\cos\theta_2}{2\sin\Delta\theta\cos\theta_1} \frac{\delta\theta}{1 + \delta\theta\cot\Delta\theta}}\right)$$ Equation 6

The transverse angle can be made large if the difference between the two Bragg angles ($\Delta\theta$) is small and the acceptance angle ($\delta\theta$) is large. An estimate of the transverse acceptance angle (a) that may occur with a non-matching monochromator crystal system can be obtained by assuming that the acceptance angle ($\delta\theta$) is the Darwin width ($\omega_D$) of the first or second monochromator crystal. Assuming for this estimation, for reason of simplicity, that both Darwin widths are approximately the same and that the two Bragg angles are close together, then:

$$a \approx 2\sin^{-1}\left(\sqrt{\frac{\cos\theta_2}{2\sin\Delta\theta\cos\theta_1}\frac{\omega_D}{1+\omega_D\cot\Delta\theta}}\right), \text{ and} \qquad \text{Equation 7}$$

$$a \approx 2\sin^{-1}\left(\sqrt{\frac{\omega_D}{2\sin\Delta\theta}}\right), \text{ and} \qquad \text{Equation 8}$$

$$a \approx 2\sqrt{\frac{\omega_D}{2\Delta\theta}}. \qquad \text{Equation 9}$$

Applying Equation 9 to a crystal monochromator including a germanium (3,3,3) crystal and a silicon (3,3,3) crystal, wherein the Darwin width of the germanium crystal is $\sim 6\times 10^{-6}$ radians and the difference ($\Delta\theta$) between the crystals is about 1 degree, at 18 keV the estimated transverse angle is about 0.05 radians, or about 2.5 degrees (corresponding to a full width of 0.1 radians or 5 degrees). This estimate matches that found with a laboratory DEI analyzer system in which the useable field of view in the transverse dimension from a line source x-ray has been found to be about 50 mm at a distance from the line x-ray source of about 500 mm. This observed transverse beam size corresponded to a full width of 0.1 radians as expected.

The second flux limiting aspect is a wavelength bandwidth limitation. When two monochromator crystals are non-matching, the energy acceptance of the crystal pair may be limited due to dispersion effects. The dispersion, or wavelength versus the diffraction angle, of a crystal is given by Equation 10, the Bragg equation, that relates the x-ray wavelength $\lambda$ to the lattice spacing for the diffraction d and the Bragg angle $\theta$ measured from the lattice planes.

$$\lambda = 2d \sin\theta \qquad \text{Equation 10}$$

Figure 2:
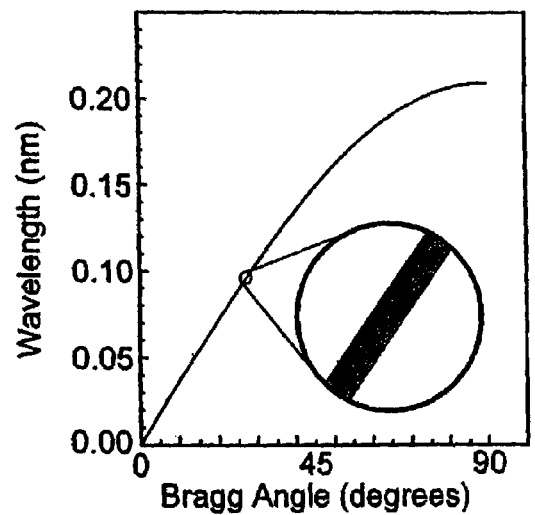
FIG. 2 is a representative DuMond Diagram of a silicon (3,3,3) crystal reflection over a Bragg angle range of 0 to 90 degrees.

This relationship can be shown in a DuMond diagram, such as the representative DuMond diagram shown in FIG. 2. FIG. 2 shows a representative DuMond diagram of a silicon (3,3,3) reflection over a Bragg angle from 0 to 90 degrees. The inset of FIG. 2 shows an enlarged region that represents the reflectivity over an angular range.

Figure 3:
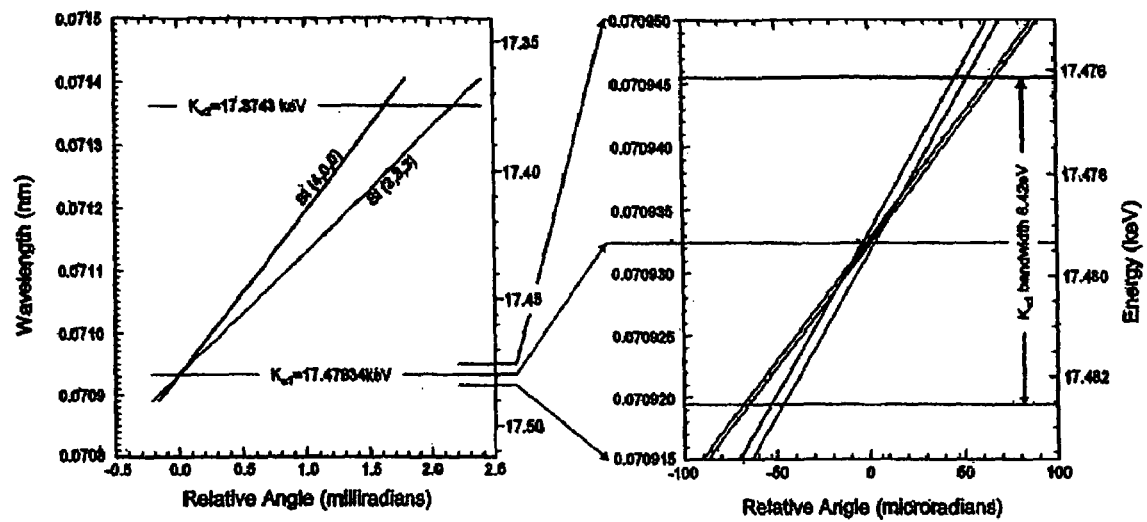
FIG. 3 is a representative DuMond Diagram of two non-matching crystal reflections, including an enlarged view of the overlap area. More particularly, the DuMond Diagram of FIG. 3 shows the overlap of dispersion curves of a silicon (4,0,0) crystal and a silicon (3,3,3) crystal.

The DuMond diagram allows a closer inspection of the dispersion curve on a scale that allows the intrinsic angular width, or wavelength or energy widths, to be observed. For a perfect crystal, this intrinsic width is the Darwin width. FIG. 3 shows a DuMond diagram of non-matching crystals. The first crystal is the silicon (3,3,3) crystal shown in FIG. 2 and the second crystal is a silicon (4,0,0) crystal. The DuMond diagram of FIG. 3 includes the second crystal as a second dispersion line. The silicon (4,0,0) crystal dispersion curve overlaps the silicon (3,3,3) crystal dispersion curve at the $K_{\alpha 1}$ emission line energy of 17.4793 keV but do not overlap at the $K_{\alpha 2}$ emission line energy of 17.3743 keV. The magnified DuMond diagram shows the overlap of the two dispersion curves in more detail. The overlap region represents the section of wavelength and angle that will be passed by the tow crystal system.

Figure 4:
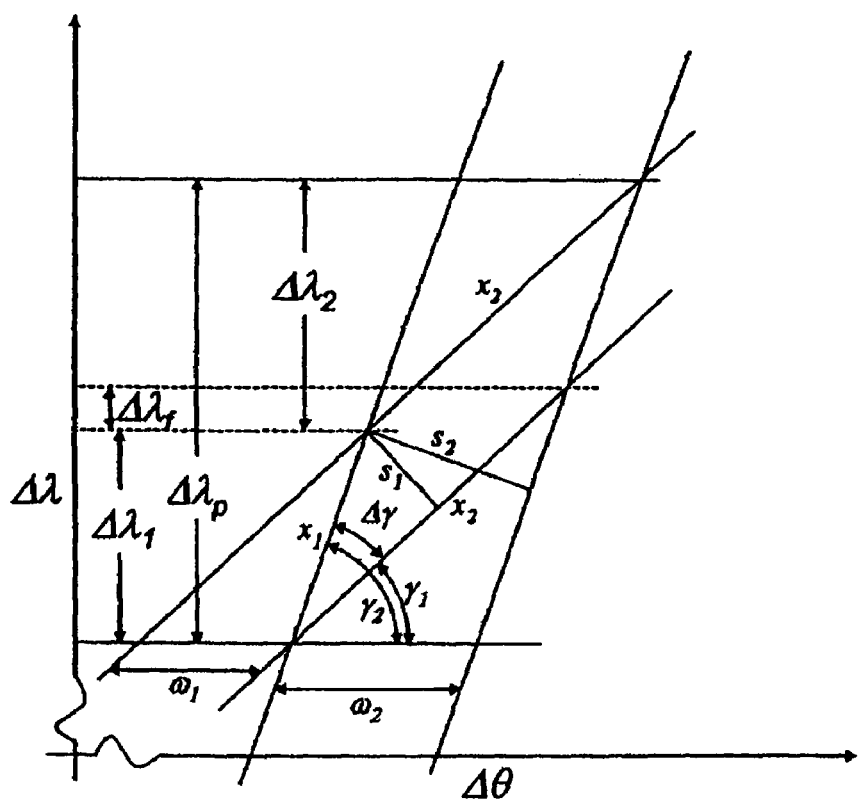
FIG. 4 is another enlarged view of the overlap area of the dispersion curves shown in FIG. 3.

FIG. 4 shows the section of the DuMond diagram where overlap occurs for dispersion curves 1 and 2. As shown in FIG. 4, the relative slope between the two DuMond plots and the widths of reflections ($\omega_1$, $\omega_2$) determine the region of overlap, or overlap area. The local slope of each dispersion curve is given Equation 11, which is a derivative of Equation 10.

$$\frac{d\lambda}{d\theta} = 2d\cos\theta \qquad \text{Equation 11}$$

As Equation 11 represents the local slope of the dispersion curve, Equation 11 will equate to the tangent of the local angle of the dispersion curve with respect to the angle axis (tan $\gamma$). The overlap area of a two non-matching crystal system is proportional to the throughput of the two crystals at the wavelength range of overlap.

The range of wavelength that is accepted is an important parameter for a line x-ray source, as the emission x-rays have a limited range of wavelengths. As seen in FIG. 4, there are four wavelength ranges: 1) a range of full overlap ($\Delta\lambda_f$); 2) a range of partial overlap ($\Delta\lambda_p$); 3) a range of overlap corresponding to the first crystal ($\Delta\lambda_1$); and 4) a range of overlap corresponding to the second crystal ($\Delta\lambda_2$). The wavelength range corresponding to the segment lengths $x_1$ and $x_2$ is determined by:

$$\Delta\lambda_{1,2} = \frac{\sin\gamma_1 \sin\gamma_2}{\sin\Delta\gamma}\omega_{1,2} = \Gamma_{1\times 2}\omega_{1,2}; \qquad \text{Equation 12}$$

where $\Gamma_{1\times 2}$ is a dispersion slope mismatch parameter defined as:

$$\Gamma_{1\times 2} \equiv \frac{2d_1 d_2 \cos\theta_1 \cos\theta_2}{d_2 \cos\theta_2 - d_1 \cos\theta_1}. \qquad \text{Equation 13}$$

Using the wavelength range for the segment length, the full and partial overlap wavelength ranges can be found as:

$$\Delta\lambda_f = \Delta\lambda_2 - \Delta\lambda_1 = \Gamma_{1\times 2}(\omega_2 - \omega_1) \qquad \text{Equation 14}$$

and $$\Delta\lambda_p = \Delta\lambda_2 + \Delta\lambda_1 = \Gamma_{1\times 2}(\omega_2 + \omega_1) \qquad \text{Equation 15}$$

As an example of this overlap, consider the silicon (3,3,3) crystal and the silicon (4,0,0) crystal of FIG. 3 at the molybdenum $K_{\alpha 1}$ line at 17.4793 keV. For these two reflections, the dispersion slope mismatch is $\Gamma_{1\times 2}=0.794$ nanometers/radian. The Darwin width ($\omega_1$) of the silicon (3,3,3) crystal is $2.9\times 10^{-6}$ radians and the Darwin width ($\omega_2$) of the silicon (4,0,0) crystal is $6.2\times 10^{-6}$ radians. Applying Equations 14 and 15, $\Delta\lambda_f = 2.7\times 10^{-6}$ and $\Delta\lambda_p = 7.2\times 10^{-6}$.

It is clear that the overlap wavelength is small and, considering Equations 13-15, that the overlap is increased by making the lattice spacing mismatch between the two crystals as small as possible. However, the mismatch must be large enough to allow the full energy band of the desired x-ray emission line to be accepted by the two crystals. As will be appreciated by one skilled in the art following the teachings herein provided, these factors can limit the lattice spacings that may be used in the two crystal monochromator system. Two possible options for non-matching monochromator crystals for use in the method of this invention include: 1) using two different crystal types, such as a silicon crystal and a germanium crystal, having identical, or at least substantially similar, lattice spacings; and 2) altering the lattice spacing of one of two crystals of the same type and having the same lattice spacing.

Figure 5:
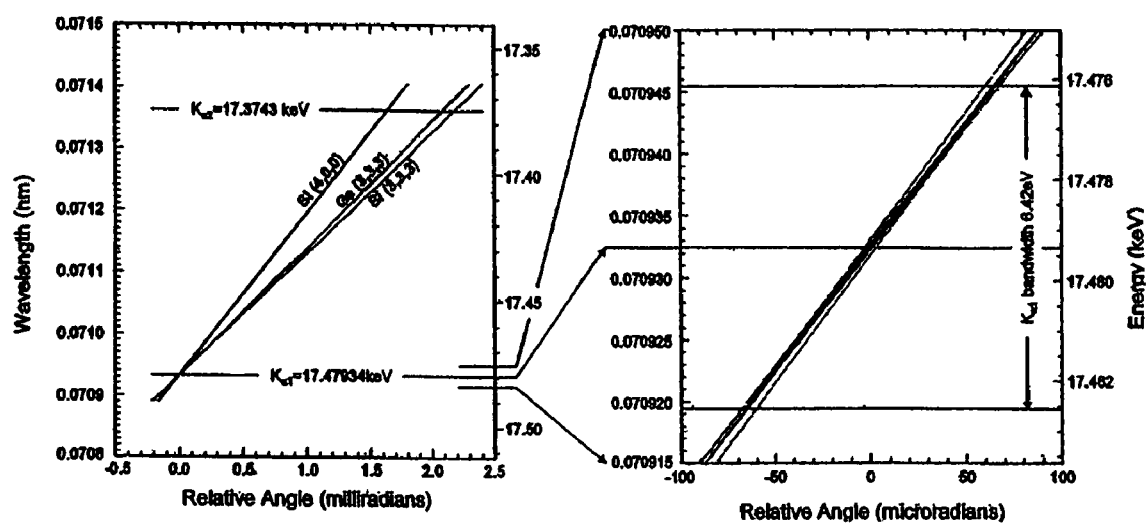
FIG. 5 is a representative DuMond Diagram of three non-matching crystal reflections, including an enlarged view of the overlap area. More particularly, the DuMond Diagram of FIG. 5 shows the overlap of dispersion curves of a silicon (4,0,0) crystal, a silicon (3,3,3) crystal, and a germanium (3,3,3) crystal.

FIG. 5 shows a DuMond diagram including the dispersion curves of the silicon crystals of FIG. 3 and a dispersion curve of a germanium (3,3,3) crystal at the same molybdenum $K_a$ wavelengths as shown in FIG. 3. The dispersion curve of the germanium (3,3,3) crystal is closer to the dispersion curve of the silicon (3,3,3) crystal than the silicon (4,0,0) crystal. For the germanium (3,3,3) crystal and the silicon (3,3,3) crystal, the dispersion slope mismatch parameter is $\Gamma_{1\times 2}=4.37$ nanometers/radian. The Darwin width ($\omega_1$) of the silicon (3,3,3) crystal is $2.9\times 10^{-6}$ radians and the Darwin width ($\omega_2$) of the germanium (3,3,3) crystal is $6.0\times 10^{-6}$ radians. Applying Equations 14 and 15, $\Delta\lambda_f=2.7\times 10^{-6}$ and $\Delta\lambda_p=7.2\times 10^{-6}$.

In one embodiment of the invention, the lattice spacing of one of two crystals of the same type and having the same lattice spacing is altered by a temperature change. For example, a silicon (3,3,3) crystal at room temperature (~25° C.) has a lattice spacing of 0.105 nanometers. To ensure that the adjacent $K_{a2}$ emission line is rejected, $\Delta\lambda_p$ should be equal to the wavelength difference between the $K_{a1}$ and the $K_{a2}$ x-ray emission lines, or $\Delta\lambda_{a1-2}$. Specifically the requirement is:

$$\Delta\lambda_{a1-2} = \Gamma_{1\times 2}(\omega_1 - e^{-BT}\omega_1) \equiv \frac{2d_1 d_1' \cos\theta_1 \cos\theta_1'}{d_1'\cos\theta_1' - d_1\cos\theta_1}\omega_1(1-e^{-BT})$$

Equation 16

The primed values are the result of lattice expansion or compression due to temperature. Assuming that $d_1'=d_1(1+\epsilon\Delta T)$, where $\epsilon$ the thermal expansion coefficient, the relationship between a lattice expansion and the Bragg angle needs to be determined to evaluate the dispersion mismatch parameter. From the Bragg relation:

$$\frac{\lambda}{2d_1} = \sin\theta_1,$$

Equation 17 then:

$$\cos\theta_1 d\theta_1 = -\frac{\lambda}{2d_1^2}dd_1,$$

Equation 18 and therefore:

$$d\theta_1 = -\frac{\lambda d_1 \epsilon \Delta T}{2d_1^2 \cos\theta_1},$$

Equation 19 or:

$$\theta_1' = \theta_1 + d\theta_1 = \theta_1 - \epsilon\Delta T\cot\theta_1.$$

Equation 20

The dispersion mismatch parameter can thus be reduced to:

$$\Gamma_{1\times 1'} \cong 2d_1\cos\theta_1 \frac{\cos\theta_1 + \epsilon\Delta T\cos\theta_1 + \epsilon\Delta T\cot\theta_1\sin\theta_1}{\epsilon\Delta T\cos\theta_1 + \epsilon\Delta T\cot\theta_1\sin\theta_1}$$

Equation 21

$$\cong 2d_1\cos\theta_1 \frac{1+2\epsilon\Delta T}{2\epsilon\Delta T}$$

$$\cong \frac{d_1\cos\theta_1}{\epsilon\Delta T}.$$

Therefore, assuming the temperature term ($e^{-BT}$) is close to unity, as is typically the case for a hard lattice such as silicon or germanium, the overall partial mismatch is:

$$\Delta\lambda_{a1-2} \cong 2\frac{d_1\cos\theta_1}{\epsilon\Delta T}\omega_1.$$

Equation 22

Solving for the temperature change to separate the lines:

$$\Delta T \cong 2\frac{d_1\cos\theta_1}{\epsilon\Delta\lambda_{a1-2}}\omega_1.$$

Equation 23

The 300K coefficient of thermal linear expansion is $4.86\times 10^{-6}$ $K^{-1}$, the wavelength difference between the $K_{a1}$ and $K_{a2}$ emission lines for molybdenum is 0.004 nanometers, and the Darwin width of a silicon (3,3,3) crystal is $2.9\times 10^{-6}$ radians. Thus, 292 K is the calculated temperature difference between the two silicon (3,3,3) crystals needed to separate the dispersion curves of the two silicon (3,3,3) crystals. This temperature difference is relatively high, but accessible.

Thus the method of this invention is a DEI method that incorporates a line x-ray source and non-matching monochromator crystals. The method of this invention provides an x-ray area beam that provides an area image of an object without a scanning system. The crystal monochromator of this invention eliminates unwanted x-ray photons from the imaging area beam and allows the use of a line x-ray source, thereby allowing use of convention x-ray tubes having relatively higher power than in conventional x-ray radiography. The higher power x-ray area beam of this invention can reduce the object imaging time and thus can reduce the x-ray exposure to the object.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A method for detecting an image of an object with an x-ray beam, the method comprising:
   diffracting the x-ray beam using non-matching monochromator crystals, the non-matching monochromator crystals including a first monochromator crystal and a second monochromator crystal, the first monochromator crystal being different from the second monochromator crystal in at least one of lattice spacing or crystal type;
   transmitting the x-ray beam from the non-matching monochromator crystals through the object;
   directing the transmitted x-ray beam at an angle of incidence upon a crystal analyzer;
   detecting a first image of the object from a diffracted beam emitted from the crystal analyzer at a first angular position of the crystal analyzer;

detecting a second image of the object from a diffracted beam emitted from the crystal analyzer at a second angular position of the crystal analyzer; and combining the first and second images to derive an enhanced image.

2. The method according to claim 1, wherein the x-ray beam is diffracted by the first monochromator crystal and the second monochromator crystal before transmitting through the object.

3. The method according to claim 1, wherein the first monochromator crystal is constructed of germanium with (3,3,3) lattice planes and the second monochromator crystal is constructed of silicon with (3,3,3) lattice planes.

4. The method according to claim 1, wherein the first monochromator crystal includes a first lattice spacing that is different from a second lattice spacing of the second monochromator crystal.

5. The method according to claim 4, wherein the first and second monochromator crystals are the same crystal type and additionally comprising heating one of the first and second monochromator crystals.

6. The method according to claim 1, wherein the x-ray beam is generated by a line x-ray source.

7. The method according to claim 1, wherein the first and second angular positions of the crystal analyzer are within a rocking curve of the crystal analyzer.

8. The method of claim 7, additionally comprising:
detecting the first image of the object at a low rocking curve angle setting of the crystal analyzer; and
detecting the second image of the object at a high rocking curve angle setting of the crystal analyzer.

9. The method according to claim 1, wherein the first image and the second image are exposed on a detector capable of producing a digitized image.

10. The method according to claim 9, wherein the exposed first image and the exposed second image are digitized.

11. The method according to claim 10, wherein the digitized images are mathematically combined to form the enhanced image.

12. The method according to claim 1, wherein the enhanced image is one of a refraction image and an absolute absorption image.

13. The method according to claim 1, wherein the crystal analyzer is one of a Bragg type analyzer and a Laue type analyzer.

14. The method according to claim 1, wherein the x-ray beam has an energy level in a range of approximately 16 keV to approximately 40 keV.

15. A method for detecting an image of an object, wherein an x-ray beam is generated, the method comprising:

generating an x-ray beam from a line x-ray source;

diffracting the x-ray beam using non-matching monochromator crystals to produce an area x-ray beam, the non-matching monochromator crystals including a first monochromator crystal and a second monochromator crystal, the first monochromator crystal being different from the second monochromator crystal in at least one of lattice spacing or crystal type;

transmitting the area x-ray beam through the object and emitting from the object a transmitted beam;

directing the transmitted beam at an angle of incidence upon a crystal analyzer;

detecting a first area image of the object from a diffracted beam emitted from the crystal analyzer at a low rocking curve angle setting of the crystal analyzer;

detecting a second area image of the object from a diffracted beam emitted from the crystal analyzer at a high rocking curve angle setting of the crystal analyzer; and combining the first area image and the second area image to derive an enhanced area image.

16. The method according to claim 15, wherein the first monochromator crystal is constructed of germanium with (3,3,3) lattice planes and the second monochromator crystal is constructed of silicon with (3,3,3) lattice planes.

17. The method according to claim 15, wherein the first monochromator crystal includes a first lattice spacing that is different from a second lattice spacing of the second monochromator crystal.

* * * * *